Figure 1:
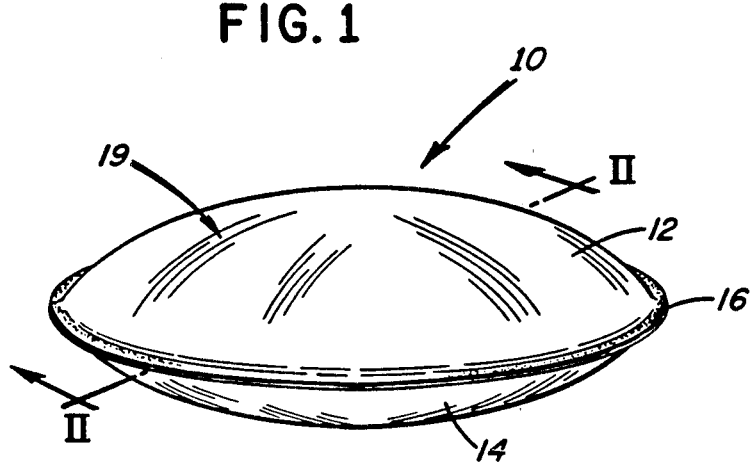

United States Patent [19]

Michelson

[11] Patent Number: 4,613,330

[45] Date of Patent: * Sep. 23, 1986

[54] DELIVERY SYSTEM FOR DESIRED AGENTS

[76] Inventor: Paul E. Michelson, 2280 Calle Tiara, La Jolla, Calif. 92037

[ * ] Notice: The portion of the term of this patent subsequent to Oct. 23, 2001 has been disclaimed.

[21] Appl. No.: 662,185

[22] Filed: Oct. 18, 1984

Related U.S. Application Data

[63] Continuation-in-part of Ser. No. 444,376, Nov. 26, 1982, Pat. No. 4,478,596.

[51] Int. Cl.⁴ .............................................. A61M 5/00
[52] U.S. Cl. .................................... 604/890; 604/893
[58] Field of Search ................................ 604/890–894

[56] References Cited

U.S. PATENT DOCUMENTS

| | | | |
|---|---|---|---|
| 2,952,023 | 9/1960 | Rosen | 3/13 |
| 3,426,754 | 2/1969 | Bierenhaum et al. | 128/156 |
| 3,641,237 | 2/1972 | Gould et al. | 424/16 |
| 3,832,458 | 8/1974 | Merrill | 424/19 |
| 3,854,480 | 12/1974 | Zaffaroni | 128/260 |
| 3,952,741 | 4/1976 | Baker | 128/260 |
| 3,967,618 | 7/1976 | Zaffaroni | 128/130 |
| 3,995,631 | 12/1976 | Higuchi et al. | 128/260 |
| 4,016,880 | 4/1977 | Theeuwes et al. | 128/260 |
| 4,057,619 | 11/1977 | Higuchi et al. | 424/14 |
| 4,077,407 | 3/1978 | Theeuwes et al. | 128/260 |
| 4,111,202 | 9/1978 | Theeuwes | 604/894 |
| 4,142,526 | 3/1979 | Zaffaroni et al. | 604/894 |
| 4,163,608 | 8/1979 | Neefe | 351/160 |
| 4,174,156 | 11/1979 | Glorieux | 351/168 |
| 4,235,236 | 11/1980 | Theeuwes | 128/260 |
| 4,265,874 | 5/1981 | Bonsen et al. | 424/15 |
| 4,298,003 | 11/1981 | Theeuwes et al. | 128/260 |
| 4,309,996 | 1/1982 | Theeuwes | 128/260 |
| 4,314,557 | 2/1982 | Chandrasekaran | 128/260 |
| 4,322,398 | 3/1982 | Reiner et al. | 424/19 |
| 4,326,525 | 4/1982 | Swanson et al. | 128/260 |
| 4,327,725 | 5/1982 | Cortese et al. | 128/260 |
| 4,340,054 | 7/1982 | Michaels | 128/260 |
| 4,466,705 | 8/1984 | Michelson | 604/893 |
| 4,478,596 | 10/1984 | Michelson | 604/890 |

FOREIGN PATENT DOCUMENTS 990164  6/1976  Canada ................................ 604/893

OTHER PUBLICATIONS

*Remington's Pharmaceutical Sciences*, 16th edition, Arthur Osol, editor, Mack Publishing Co., 1980, pp. 182–193, "Complexation", Chapter 14, by Gennaro.
*Physical Pharmacy*, 2d edition, Martin et al, Lea & Febiger, 1969, pp. 325–351, "Complexation", Chapter 13.

*Primary Examiner*—C. Fred Rosenbaum
*Assistant Examiner*—Sherri Vinyard
*Attorney, Agent, or Firm*—Spencer & Frank

[57] ABSTRACT

A system for the controlled delivery of a desired agent to a fluid environment. A semipermeable container defines a fully enclosed cavity and is imperforate except for a plurality of pores for permitting fluid to flow from the fluid environment into the cavity. A quantity of a molecular complex is positioned in the cavity. The molecular complex comprises a macromolecule that is non-diffusable with respect to the container and a desired agent complexed to the macromolecule, the agent being capable of dissociating from the macromolecule over time. The pores of the container have a larger size in relation to the agent and the container is so constructed as to permit unimpeded passage of the agent through the pores. The concentration of the agent within the cavity is controlled by the equilibrium between the molecular complex and the agent within the cavity and the active agent is deliverable by the system to the fluid environment exclusively through the plurality of pores.

16 Claims, 3 Drawing Figures

DELIVERY SYSTEM FOR DESIRED AGENTS

RELATED APPLICATIONS

This is a continuation-in-part of U.S. patent application Ser. No. 06/444,376 filed Nob. 26th, 1982, now U.S. Pat. No. 4,478,596. Further, this application is related to U.S. patent application Ser. No. 06/432,409, filed Sept. 30th, 1982, now U.S. Pat. No. 4,466,705, and U.S. patent application Ser. No. 06/639,480, filed Aug. 10th, 1984, which is a continuation-in-part of U.S. patent application Ser. No. 06/432,409, the disclosures of which are incorporated herein by reference.

The present invention relates generally to an improved system for the controlled delivery of a desired agent to a medium in which the agent is soluble or diffusible.

In recent years numerous devices have been devised which utilize osmotic flow to assist in the delivery of desired agents, such as physiologically active agents. For example, both U.S. Pat. No. 4,265,874 to Bosen et al and U.S. Pat. No. 4,298,003 to Theeuwes et al disclose methods and devices for the delivery of a drug where, as a result of osmotic flow, fluid passes through a semipermeable membrane and forces an insoluble drug or a solution of a soluble drug out of the device through an enlarged opening or passageway. The membrane of these devices allows the flux of water only, not the drug. The drug is forced out, under the influence of osmosis, through the enlarged opening or passageway which is separately drilled in the devices and whose size is orders of magnitude larger than the pores of the membrane.

U.S. Pat. No. 3,832,458 reveals a device in which a silicon polymer wall is utilized to vary permeability to an internal active agent. The permeability is adjusted by fabricating the wall with varying amounts of N-vinylpyrrolidone. While this device represents an improved delivery technique, it has a significant disadvantage in that it represents a "first order" delivery system in which the driving force of drug delivered to the outside is the result of the internal concentration of drug along. Thus the drug will be delivered at an initial rapid rate followed by a significantly lower rate until the active agent is expended.

U.S. Pat. No. 4,309,996 by Theeuwes discloses a somewhat different mechanism for delivery of drugs whereby a separate compartment filled by a net osmotic inflow is utilized to expand against a flexible internal partition which forces active agent out of a second compartment through a microporous structure, thus attempting to approximate a steady delivery rate.

While known prior art devices have resulted in improved delivery techniques, they are either somewhat complex, adding to the cost of the devices, or unable to control the precise delivery rate of the desired agent. It is therefore advantageous to provide a system which is flexible in that there are numerous variables which can be modified to control the delivery rate of the desired agent.

SUMMARY OF THE INVENTION

It is an object of the present invention to provide a new and improved system for delivering a desired agent to a medium in which the agent is soluble or diffusible.

It is a further object of the present invention to provide a new and improved system for the delivery of a desired agent which is less complex than prior art devices.

It is an additional object of the present invention to provide a new and improved system for the delivery of a desired agent which permits more control and flexibility in the amount and rate of delivery of the agent than prior art devices.

It is another object of the present invention to provide a new and improved system for the delivery of a desired agent which utilizes the pores of a semipermeable container to deliver the agent to a surrounding fluid environment.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a system for the controlled delivery of a desired agent to a fluid environment, the system including a semipermeable container defining a fully enclosed cavity and being imperforate except for a plurality of pores for permitting the flow of fluid from the fluid environment into the cavity; and a quantity of a molecular complex positioned in the cavity. The molecular complex comprises a macromolecule that is nondiffusible with respect to the container and a desired agent complexed to the macromolecule, the agent being capable of dissociating from the macromolecule over time. The pores have a larger size in relation to the agent and the container is so constructed as to permit unimpeded passage of the agent through the pores. The concentration of the agent within the cavity is controlled by the equilibrium between the molecular complex and the agent within the cavity and the agent is deliverable by the system to the fluid environment exclusively through the plurality of pores.

In a preferred embodiment of the invention the container comprises a semipermeable sheath.

Additionally, in a further aspect of the invention the container is biodegradable.

BRIEF DESCRIPTION OF THE DRAWINGS

FIG. 1 is a perspective view of a system according to the invention.

FIG. 2 is a sectional view along the section line II—II in FIG. 1.

FIG. 3 is a plot of the drug delivery rates of systems according to the invention.

DESCRIPTION OF THE PREFERRED EMBODIMENTS

In accordance with the invention, as shown in FIG. 1, a device 10, which is generally of circular configuration, but whose shape may vary as appropriate for differing sites of application, consists of a semipermeable container, preferably in the form of a sheath 19 which is made of two thin sheets 12 and 14. The thin sheets 12 and 14 are bound along their respective edges to form a sheath with an outside edge 16. As will be apparent hereinafter, the delivery system according to the invention, is intended to be used in a fluid environment with sufficient fluid present to enable the system to operate as intended. Preferably, the environment is completely and consistently composed of a fluid medium in which a desired agent is soluble or diffusable; however, the environment could be partially filled or intermittently filled with the fluid medium. The system according to the invention, is particularly suitable for the delivery of active agents to animals and may be located with respect to the animal to be treated by positioning or implanting the system in a variety of locations such as the animal's rectum or gastro-intestinal tract, etc.

Figure 2:
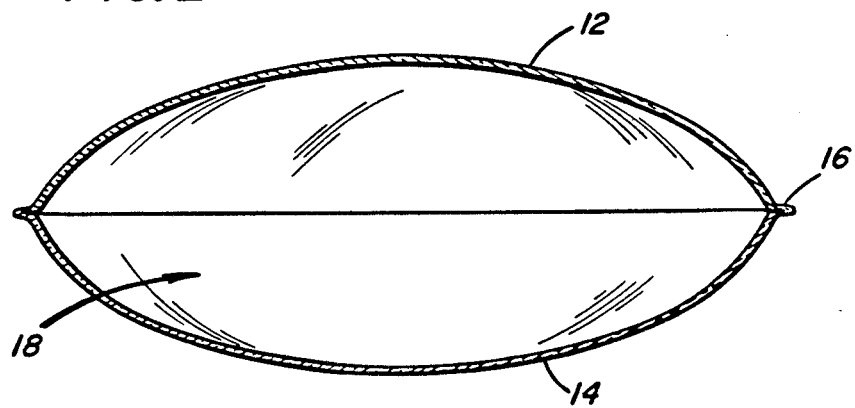

As can be seen in FIG. 2, thin sheets 12 and 14 define a cavity 18 which is intended to contain a desired agent for delivery to a selected environment. Thin sheets 12 and 14 are provided with a plurality of pores in order to be semipermeable and permit the passage of fluid therethrough. The semipermeable thin sheets 12 and 14, when joined to form edge 16, result in a semipermeable sheath.

The present invention utilizes the principle of osmotic flow which results from a difference in molecular concentration being present across a semipermeable membrane.

According to the invention, cavity 18 will contain at least one desired agent which will go into solution with fluid which will enter cavity 18. The agent may or may not be fully soluble as long as it can be delivered from device 10 at a suitable and predictable rate. As will be described in more detail hereinafter, in a preferred embodiment of the invention, a macromolecule may also be present in cavity 18. The term macromolecule is intended to mean a large molecule such as a protein, carbohydrate, rubber or other natural or synthetic high polymer or a polymer array including a hydrophilic polymer array (commonly referred to as a hydrogel).

The presence of the desired agent in cavity 18 results in a net molecular concentration gradient being set up between the cavity 18 and the fluid environment in which the delivery system is used. This net molecular concentration gradient will result in flow of fluid from the fluid environment through the semipermeable sheath into cavity 18. This flow of fluid, generally referred to as osmotic flow, results from the net higher molecular concentration or net higher osmotic pressure which is present in cavity 18 due to the presence of the desired agent alone or the agent and the macromolecule. That is, the body of fluid inside the semipermeable sheath is hypertonic with respect to the fluid outside of the semipermeable sheath, i.e. the fluid inside the semipermeable sheath has a higher osmotic pressure than the fluid outside the semipermeable sheath.

When measured at any given instance, the osmotic pressure inside cavity 18 will be higher than that of the fluid surrounding the device and, therefore, there will be a net inward flow of fluid. However, over a period of time fluid continuously enters and leaves cavity 18 which results in a dispersion of the agent from cavity 18. While there will be continuing "steady-state" flux of fluid between the environment and internal fluid of the device, the net inflow of fluid volume will occur in the initial states under the influence of osmosis until the osmotic pressure and fluid inflow result in the device achieving its natural premolded configuration. The burst strength of the encapsulating polymer film and its seal exceed the maximum achievable osmotic pressure by at least several orders of magnitude. The continuing steady-state flux of fluid across the walls of the device will result in the dispersion of any agent whose molecular size is such as to allow passage through the preselected pore diameter of the membrane wall.

The osmotic flow which results due to molecular concentration differences is independent for each molecule involved. For example, in the above example if the macromolecule, designated A, and another molecule, designated B, were added to cavity 18, and went into solution and became part of the body liquid 19, molecule B would set up a concentration gradient across the semipermeable sheath independent of the gradient present as a result of macromolecule A. The osmotic flow resulting from the presence of molecule B would be independent of the osmotic flow resulting from the presence of macromolecule A.

In a preferred embodiment of the invention a macromolecule would be complexed with a desired agent and the macromolecule selected such that it would be larger than the pores of the semipermeable sheath, yet the complex would decay over a period of time thereby allowing the agent to slowly disperse from the semipermeable sheath.

A given delivery rate of desired agent and/or complexing molecule can be achieved through selection of appropriate membrane pore size, density, environmental conditions and binding macromolecule. The desired agent and binding macromolecule form a molecular complex with an affinity for each other which can be expressed as an association constant, an easily determined quantity related to concentration and physicochemical environment. This constant is directly proportional to the concentration of the complex and inversely proportional to the product of the concentrations of desired agent uncomplexed and binding macromolecule uncomplexed. It can thus be seen that if a nondiffusible binding macromolecule is chosen, the further dampening of a potentially rapid or exponential rate of delivery of desired agent can be achieved. In simple form, if the association constant is represented as K, the molar concentration of the desired agent as (D), the binding macromolecule concentration as (B), and the bound complex as (B−D), the following represents the relationship described: $K = (B-D)/(B)(D)$.

The thickness of the semipermeable sheet material, utilized in connection with the invention, will depend on a number of factors and is directly related to the intended use of the delivery system. Generally, the membrane thickness will range from 5–10 micrometers, depending upon the material used and the intended configuration and concentration gradient.

Material for the semipermeable sheath for the desired agents could be composed of nondegradable, nonabsorbable materials with long useful lifetimes such as cellulose acetate, cellulose acetate butyrate, cellulose triacetate, poly-1, 4 butylene terephthalate (such as MYLAR ®), polymethylmethacrylate, polypropylene (such as CRYOYAC ®), polystyrene, polyvinyl acetate, polyvinyl chloride, polyvinyl fluoride, polyvinylidene chloride (such as SARAN ®), polycarbonate or silicon-polycarbonate copolymers (such as NUCLEPORE ®) and others.

Alternatively, and depending on the intended use, the sheath could be fabricated from biodegradable or absorbable polymer films designed for degradation and/or absorption subsequent to the planned useful life of the delivery system. Examples of such biodegradable films are cellulose, collodion, polyvinyl pyrrolidone, polyamides, polylactide and polyglycolide.

The macromolecule, according to the invention, may be selected from any class of compounds with molecular weight and configuration sufficiently large to be excluded passage by the desired pore size. Generally suitable are the dextrans, amylopectins (hydroxyethylstarch), polyvinylpyrrolidone, polyethylene glycol, albumin and various other soluble polymers and/or proteins. Alternatively, emulsions with droplets containing active agent can be utilized as well. Microemulsions with droplets of a diameter range 0.01 to 0.1 microns are transparent and optically clear and thus, preferable for optical systems whereas macroemulsions with droplets of size 0.1 to 1 or 2 micrometers may be satisfactory in other uses. Also suitable as the complexing macromolecule are hydrogels such as those identified in applicant's copending U.S. patent application Ser. No. 06/639,480.

The agents for delivery according to the invention can include, but are not limited to, examples from 10 the following categories: biologically or physiologically active agents such as pharmaceuticals, vitamins, enzymes, coenzymes and minerals; industrially and commercially useful agents such as lubricants, chelating agents, catalysts, preservatives, soaps, surfactants, biocides, pesticides, germicides, insecticides, and miscellaneously useful agents such as fertilizers, adjuvants and enzyme inhibitors.

Agents which could be used in connection with the present invention include for example: oxygen, preferentially bound to fluorocarbons; salicylates, catechols, halogens, barbiturates or other compounds complexed to a macromolecule such as polyethylene glycols; antibiotics such as chloramphenicol, sulfa or other medications complexed with a macromolecule such as polyvinylpyrrolidone; antiepileptic medications such as phenytoin complexed to albumin; antihistamines, quinine, procaine or other compounds complexed to a macromolecule such as sodium carboxymethylcellulose; salicylates complexed to the antibiotics oxytetracycline or tetracycline or other compounds complexed to a macromolecule such as salicylates; or, other macromolecules could be utilized such as caffeine or albumin. The above identified complexes have well known association constants. See generally *Remington's Pharmaceutical Sciences*, 16th Edition, Arthur Osol, Editor, Mack Publishing Co. 1980, pp. 182-193 and *Physical Pharmacy*, 2nd Edition, Martin et al, Lea & Febiger, 1969, pp. 325-352.

The delivery system according to the invention can be used in a variety of ways and can take various forms, depending on the agent being delivered and the particular environment. For example, a polymer sheath fitted comfortably into the conjunctival cul-de-sac of the eye could be used to deliver ophthalmic drugs such as pilocarpine, epinephrine, Timolol, various antibiotics and other topically useful ophthalmic drugs.

An appropriately shaped delivery system according to the invention with a possibly biodegradable sheath could be inserted into the uterus and/or vagina and used to deliver progesterone and/or estrogen hormones for birth control or fungicides for infection. Further, an appropriately shaped and potentially biodegradable sheath for placement in the urinary bladder, the rectum, oropharynx or nasopharynx or other areas of the gastrointestinal track could be used to deliver antispasmodics, anti-infectives or other pharmaceuticals. Additionally, an appropriately shaped sheath could be used according to the invention to deliver anti-asthmatic or other pulmonary and/or cardiac drugs through mucous membranes.

A delivery system according to the invention could also take the form of a skin patch for transdermal delivery of drugs such as Scopolamine, aspirin and nitroglycerin.

The delivery system according to the invention could also be used as an intracavity implantation at the time of surgery for the delivery of drugs such as antibiotics, chemotherapeutic agents for the control of cancer, anticoagulants and other pharmaceuticals or active agents. For example, an intracavitary implantation comprising the delivery system according to the invention could be used to deliver a chemotherapeutic agent being placed within the abdominal cavity at the time of operation when metastatic or potentially unexcised cancer exists, or to deliver anticoagulants about a vascular graft or area of diagnosed past or potential thrombosis, or to deliver insulin or other hormone or pharmaceutical or other agent for release from a subcutaneous or other operative site.

The delivery system according to the invention may also be used in ponds or other bodies of water or included in soil or other environments in which solubility and/or diffusion is possible for the delivery, from a possibly biodegradable container, of fertilizers, pesticides, fungicides and other environmentally active agents. Examples of such agents include algicides for use in swimming pools, 2-mercaptobenzothiazole for slime control during paper and textile processing, pentachlorophenol and other antifungal agents to prevent degradation of cellulose derivatives, malathion and other pesticides, formaldehyde and naphthol.

The sheets which comprise the sheath according to the preferred embodiment of the invention can be made porous in a variety of ways. For example, the technique of nuclear track etching can be used, in which the polymer films are exposed to radioactive decay particles and products and then treated chemically to "etch" permanently the tracks of the particles through the film, thus creating pores of a size and density determined by the exposure time and etching process. The particle dose determines the hole density while the pore diameter is a function of etching time. The specific particles, dose, etchants, and other conditions to achieve desired pore sizes and density for the aforementioned polymer films are well known in the prior art. See *Nuclear Tracks in Solids, Principals and Applications*, R. L. Fleischer et al, University of California Press, 1975. For example, polycarbonate filters (such as NUCLEPORE ®) are produced by exposure to $U^{235}$ followed by sodium hydroxide etching. Polyvinylidene chloride (such as SARAN ®) can be made microporous by exposure to fission fragments of Californium 252 followed by etching with potassium permanganate at 55 degrees Centigrade. As an alternative to nuclear tracking etching, the newer advanced lasers such as frequency-doubled Neodymium-YAG, Excimer, tunable dye or other lasers may be used to produce pores of the desired size and density.

Pores may also be created by forming membranes as integrated sheets of polymer containing "pore-formers," molecules which subsequently can be leached or dissolved out, leaving a predictable pore size. The leaching or dissolution can be accomplished prior to use or so selected to occur in the environment of use. For example, certain polymer films made of various polycarbonates, polyamides, or polyesters can include such pore formers as lithium carbonate, calcium phosphate, various polysaccharides, such as mannitol, CARBOWAX ®, etc. These above processes, and others for creating microporous membranes, are noted in the prior art literature and are compiled in such works as *Synthetic Polymer Membranes* by R. E. Kesting, McGraw-Hill, Inc., 1971.

The pore size will preferably range between 50 Angstroms diameter to 1,000 Angstroms; however, it may be possible to have pore sizes smaller than 50 Angstroms, if desired. The pore size is selected depending on the molecular weight and configuration of the macromolecule. For example, a pore size of approximately 60 Angstroms will exclude a molecule having a molecular weight of about 10,000. A 100 Angstrom pore size will exclude a molecule having a 100,000 molecular weight. The exact three dimensional configuration of the molecules may, of course, produce exceptions. Pore density would be on the order of $10^5$ to $10^{10}$ per square cm; however, depending on the application of the device, pore densities less than $10^5$ per square cm may be used.

The thin sheets 12 and 14 may be joined at their respective edges to form edge 16 in a variety of ways. Various heat and impulse sealers can be used with variations in temperatures, frequency, and times allowing for substantial flexibility depending upon the particular polymer. Various one-part and two-part compatible adhesive bonding systems such as EASTMAN 910®, EPON 828® and 3M CONTACT CEMENT® could also be used. In addition, some materials are suitable for bonding without using conventional bonding methods. For example vinylidene chloride may be sealed to itself while in the so-called "supercooled" state to form a strong bond without conventional dielectric heat or adhesive methods.

Osmotic pressures generated in cavity 18 obviously will be significantly less than the burst strength of the semipermeable membranes. For example, the pressure generated by the macromolecule will be in the order of less than 0.34 atmosphere (5 pounds per square inch), while, for example, the burst strength of vinylidene chloride 1 mil thick is 30 pounds per square inch.

The following specific examples of delivery systems, in accordance with the invention, are set forth as illustrative only, and should not in any way limit the scope and purpose of the present invention.

A delivery system for the drug phenytoin, is constructed by forming a sheath made from planar sheets of polycarbonate membrane, with pore size of 0.015 micrometers, porosity $12 \times 10^8/cm^2$ and thickness 6 micrometers. The polycarbonate membrane is heated to 220 degrees centigrade, and molded by vacuum or pressure to a spherical cap of 6.0 mm diameter with radius of curvature, 6.4 mm. A ½ mm wide planar circumferential cuff is left about each empty spherical cap. Then, 25 µg of phenytoin, along with 100 µg of albumin are placed into one cap after which the opposing cap is utilized as a cover and the circumferential cuff of ½ mm is sealed together at 230–275 degrees centigrade. This creates an envelope of potential volume 11.92 cu mm. Placed in the fluid environment of use, the delivery system will fill to its normal volume.

FIG. 3 is a plot of the delivery rate of systems according to the invention comparing the delivery rate of a system containing phenytoin-albumin complex with the delivery rate of a system containing phenytoin alone. In the first half-hour the system utilizing the drug phenytoin-albumin complex shows that 0.74% of its drug content by weight will have been expended and after one hour a total of 1.7% will have been expended, and so on for the following intervals: 2 hrs, 3.4%; 4 hrs, 5.4%; 10½ hrs, 12%; 24 hrs, 20.2%; 33½ hrs, 27.2%.

By contrast, an identical device containing only phenytoin without albumin will deliver at the identical time intervals as noted above, the following percentages of the initial amount of drug placed in the device: ½ hr, 1.47%; 1 hr, 2.97%; 2 hrs, 5.7%; 4 hrs, 9.6%; 10½ hrs, 22.4%; 24 hrs, 38%; 33½ hrs, 47.2%.

According to a further aspect of the invention an additional control factor for the delivery rate of a desired agent can be introduced by employing two or more complexes of the same desired agent. That is, the agent to be delivered is involved in a complex with more than one variety of macromolecule. If the complexes have different association constants, the delivery rate is then a resultant of the chemical equilibria established for all complexes of the beneficial agent. For example, a desired agent such as caffeine or various sulfa drugs may be complexed with both albumin and p-aminobenzoic acid, each such complex having a different association constant. Another example is sulfadiazene complexed respectively with caffeine-like compounds and albumin, again each complex having a different association constant under similar physical-chemical environments. With the use of more than one complexing macromolecule within the cavity, an additional, predictable and calculable parameter is introduced as a means to program the exact delivery profile.

According to a further aspect of the invention, a delivery system constructed according to the principles of the invention can be desirably employed to interact with the environment in a feedback loop arrangement wherein the delivery of the agent to the environment is dependent upon the concentration of the agent in the environment capable of diffusing into the container and reacting with the binding site of the macromolecule. Such an arrangement would arise when, for example, the delivery system of the invention is immersed in a fluid environment which already contains a certain concentration of the agent to be delivered or in which the agent being delivered is not constantly metabolized or otherwise removed from the environment. In such a case, the environment represents a reservoir of varying concentrations of the desired agent. Since the pores of the container according to the invention are larger in size than the desired agent, the agent can move unimpeded into or out of the container, dependent upon the relative concentrations of the agent within and outside the container. If the concentration of the desired agent is greater outside the container, the agent may enter the container through the pores and interact with the complexing molecule just as the resevoir of free agent within the container interacts to influence the dissociation/association of additional agent from the macromolecule One particularly advantageous use of a delivery system according to the invention in a feedback loop arrangement concerns the use of the delivery system as a fluid contact lens or a fluid intraocular lens of the type described in U.S. Pat. No. 4,466,705, and U.S. patent application Ser. No. 06/639,480. In such a lens a macromolecule is positioned within a cavity defined by a semipermeable sheath to set up an osmotic gradient. Liquid in the environment thus flows into the sheath under the influence of osmosis, causing the sheath to assume a predetermined shape. The sheath is transparent and the body of fluid in the sheath's cavity constitutes a fluid lens. If the macromolecule in the body of liquid within the sheath is, for example, a polymerized bovine hemoglobin, pyridoxylated hemoglobin or other similar oxygen-carrying molecule, the lens can additionally be utilized as a delivery system for delivering oxygen molecules to the fluid environment of the eye. The amount of oxygen released from the carrier molecules would be dependent on the oxygen within the delivery device, i.e. the lens, but the amount of oxygen within the device is also in equilibrium with the oxygen in the fluid environment. The concentration of oxygen in the fluid environment changes from the normal ambient partial pressure of oxygen in the environment when the eyes are opened to a much lower level when the eyes are closed during sleep. Thus, the amount of oxygen released from the lens/delivery system fluctuates depending upon the concentration of oxygen in the environment and is consistent with needs of the cornea.

The delivery rate of the desired agent according to this aspect of the invention also may be influenced by other agents in the environment which are capable of diffusing into the container of the delivery system and competing with the desired agent for the binding site of the macromolecule. For instance, in the foregoing example of the lens/delivery system, competitive binding may occur with carbon dioxide which is liberated from the eye and which diffuses into the delivery container. Carbon dioxide, being similar to oxygen in its affinity for the complexing hemoglobin macromolecule, is capable of displacing oxygen from the macromolecule. Thus, with the eye in the closed position, it may be appreciated that carbon dioxide builds up in the fluid environment of the lens, resulting in more carbon dioxide diffusing into the interior of the lens and displacing oxygen from its carrier macromolecule. The displaced oxygen then diffuses by osmosis into the fluid environment which, because the eye is closed, is oxygen deficient. When the eye is opened, the higher level of carbon dioxide is reduced by free exchange with the atmosphere, and of course, an increased available oxygen pressure allows resaturation of the complexing hemoglobin macromolecule.

Other examples of agents which can compete for binding sites on a macromolecule and which could be used in beneficial fashion to program a given delivery profile for a delivery system according to the invention include: sulfonamides competing with phenylbutazone for a binding site on an albumin macromolecule; warfarin and similar anticoagulants competing with phenylbutazone for a binding site on an albumin macromolecule; triiodothyronine competing with ethylchlorophenoxyisobutyrate in its binding with albumin; and atropine in competition with acetyl choline-like drugs for protein binding.

Thus, in accordance with this last aspect of the invention, a delivery system is provided in which the delivery rate of the desired agent is influenced not only by the intrinsic concentration of the agent which is initially placed within the delivery container, but also by the concentration of desired agent and similar agents capable of competing with the desired agent for the binding site of the macromolecule existing in the environment and thus influencing the overall delivery rate and profile of the delivery system.

It will be understood that the above description of the present invention is susceptible to various modifications, changes and adaptations, and the same are intended to be comprehended within the meaning and range of equivalents of the appended claims.

What is claimed is:

1. A system for the controlled delivery of a desired agent to a fluid environment comprising:
a semipermeable container defining a fully enclosed cavity and being imperforate except for a plurality of pores for permitting the flow of fluid between the fluid environment and said cavity; and
a quantity of molecular complex positioned in said cavity, said molecular complex comprising a macromolecule that is nondiffusable with respect to said container and a desired agent complexed to said macromolecule, said agent being capable of dissociating from said macromolecule over time, said pores having a larger size in relation to said agent and said container being so constructed as to permit unimpeded passage of said agent through said pores, wherein the concentration of said agent within said cavity is controlled by the equilibrium between said molecular complex and said agent within said cavity and said agent is deliverable by said system to the fluid environment exclusively through said plurality of pores.

2. The system according to claim 1, wherein said container is biodegradable.

3. The system according to claim 1, wherein said container comprises a semipermeable sheath.

4. The system of claim 1, wherein said sheath has a thickness of less than 50 microns.

5. The system of claim 1, wherein the diameter of said pores is less than 1,000 Angstroms.

6. The system of claim 1, wherein said container has a pore density between 100 and $10^{10}$ pores per square cm.

7. The system of claim 1, wherein said pores are sufficiently small to prevent the passage therethrough of said macromolecule.

8. The system of claim 1, wherein said container is transparent and said macromolecule is photostable.

9. The system of claim 1, wherein said macromolecule is inert.

10. The system of claim 1, wherein said macromolecule is selected from a group consisting of protein, cellulose, carbohydrates, rubber, high polymers and polymer arrays.

11. The system of claim 1, wherein said macromolecule is hydrophilic.

12. The system of claim 1, wherein said quantity of molecular complex constitutes a quantity of a first molecular complex with comprising a macromolecule of a first type complexed said desired agent, and said system further includes a quantity of a second molecular complex comprising a macromolecule of a second type that is nondiffusable with respect to said container and said desired agent complexed with said macromolecule of the second type, said desired agent being capable of dissociating from said macromolecule of the second type, and said first and second molecular complexes having different dissociation constants, wherein the concentration of said desired agent within said cavity is controlled by the equilibria between said desired agent and said first and second molecular complexes, respectively.

13. The system of claim 1, in combination with a fluid environment which contains a varying concentration of the desired agent, wherein the desired agent freely flows into and out of said cavity through said pores dependant upon the relative concentration of said agent within said cavity and in said environment.

14. The system of claim 1, in combination with a fluid environment which contains a second agent which can diffuse into said cavity through said pores for influencing the delivery of said desired agent to the environment, wherein said macromolecule is susceptible to competitive binding by said second agent and said second agent causes said desired agent to dissociate from said macromolecule and said second agent complexes with said macromolecule in place of said desired agent.

15. The system according to claim 1, wherein said desired agent is oxygen and said macromolecule complexes with oxygen molecules.

16. The system according to claim 1, wherein said macromolecule is hemoglobin and said desired agent is oxygen.

* * * * *

UNITED STATES PATENT AND TRADEMARK OFFICE
CERTIFICATE OF CORRECTION

PATENT NO. : 4,613,330

DATED : September 23, 1986

INVENTOR(S) : Paul E. Michelson

It is certified that error appears in the above-identified patent and that said Letters Patent is hereby corrected as shown below:

<u>IN THE DRAWINGS</u>

Add Figure 3 as shown.

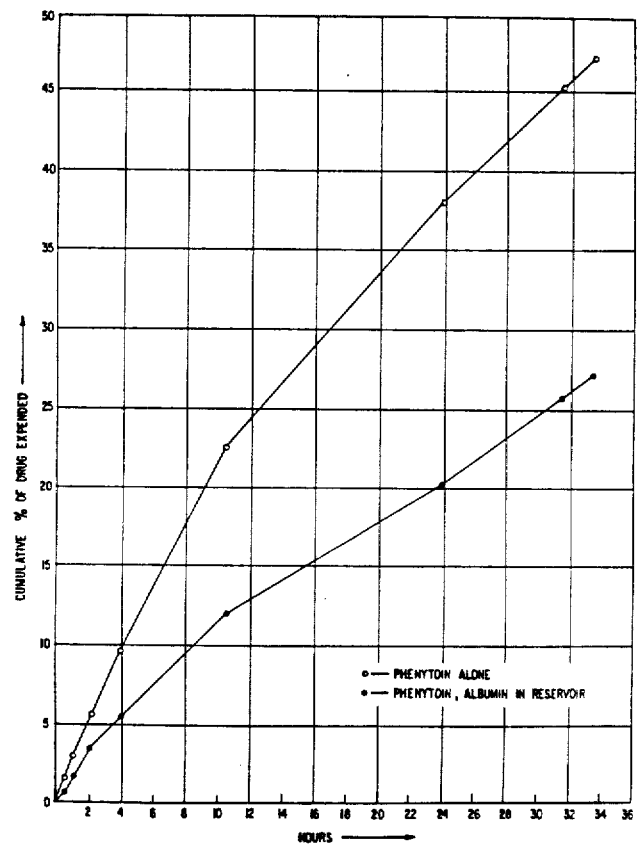

FIG. 3

UNITED STATES PATENT AND TRADEMARK OFFICE
CERTIFICATE OF CORRECTION

PATENT NO. : 4,613,330

DATED : September 23, 1986

INVENTOR(S) : Paul E. Michelson

It is certified that error appears in the above-identified patent and that said Letters Patent is hereby corrected as shown below:

Column 1, line 6, change "Nob." to --Nov.--.

IN THE CLAIMS

Claim 12, line 3, delete "with".

Claim 12, line 4, after "complexed" insert --with--.

Signed and Sealed this

Seventeenth Day of February, 1987

*Attest:*

DONALD J. QUIGG

*Attesting Officer*　　*Commissioner of Patents and Trademarks*